US010953238B2

(12) United States Patent
Alvarez et al.

(10) Patent No.: US 10,953,238 B2
(45) Date of Patent: Mar. 23, 2021

(54) DERMAL REPAIR MANAGEMENT DEVICES

(71) Applicant: ALVALUX MEDICAL,
Hermalle-sous-Argenteau (BE)

(72) Inventors: Michel Alvarez,
Hermalle-sous-Argenteau (BE); Denis Flandre, Brussels (BE)

(73) Assignee: ALVALUX MEDICAL, Liège (BE)

( * ) Notice: Subject to any disclaimer, the term of this patent is extended or adjusted under 35 U.S.C. 154(b) by 164 days.

(21) Appl. No.: 16/088,666

(22) PCT Filed: Mar. 27, 2017

(86) PCT No.: PCT/EP2017/057200
§ 371 (c)(1),
(2) Date: Sep. 26, 2018

(87) PCT Pub. No.: WO2017/167693
PCT Pub. Date: Oct. 5, 2017

(65) Prior Publication Data
US 2019/0076669 A1 Mar. 14, 2019

(30) Foreign Application Priority Data
Mar. 31, 2016 (EP) ..................................... 16163146

(51) Int. Cl.
*A61N 5/06* (2006.01)

(52) U.S. Cl.
CPC .... *A61N 5/0616* (2013.01); *A61N 2005/0645* (2013.01); *A61N 2005/0651* (2013.01);
(Continued)

(58) Field of Classification Search
CPC .......... A61N 5/0616; A61N 2005/0645; A61N 2005/0651; A61N 2005/0653; A61N 2005/0659; A61N 2005/0662
See application file for complete search history.

(56) References Cited

U.S. PATENT DOCUMENTS 5,616,140 A * 4/1997 Prescott ............... A61N 5/0616
606/10
2004/0054386 A1* 3/2004 Martin ................. A61N 5/0616
607/88
(Continued)

FOREIGN PATENT DOCUMENTS

WO WO2014146029 A1 9/2014
WO WO2016007798 A3 1/2016

OTHER PUBLICATIONS

European Patent Office search report dated Jul. 21, 2017 re PCT Application No. PCT/EP2017/057200 of Alvalux Medical.

*Primary Examiner* — Ankit D Tejani
*Assistant Examiner* — Joshua Brendon Solomon
(74) *Attorney, Agent, or Firm* — Daugherty & Del Zoppo Co. LPA.

(57) ABSTRACT

This invention provides for a dermal repair system including a dermal repair device which is configured to be placed on the skin of a user. The dermal repair device is in the form of a removable silicone sheet which can be securely fixed in place and re-used after cleaning etc. The silicone sheet includes sheet sections and a housing section into which a rechargeable control unit can removably be inserted. Waveguides in the form of a dimple teardrop pattern are provided for directing radiation or light to distal ends of the sheet. The control unit includes a low-level radiation or light source from which radiation or light is directed along the sheet for a therapy regimen to treat closed wounds and scars, such as, C-section and breast surgery closed wounds and scars to improve healing and scar appearance. The system further comprises a recharging station configured for recharging the control unit.

26 Claims, 10 Drawing Sheets

(52) U.S. Cl.
CPC .............. *A61N 2005/0653* (2013.01); *A61N 2005/0659* (2013.01); *A61N 2005/0662* (2013.01)

(56) References Cited

U.S. PATENT DOCUMENTS

| | | | |
|---|---|---|---|
| 2007/0208395 A1* | 9/2007 | Leclerc | A61N 5/0616 607/86 |
| 2007/0233208 A1 | 10/2007 | Kurtz et al. | |
| 2007/0239232 A1* | 10/2007 | Kurtz | G02B 6/001 607/87 |
| 2008/0269849 A1* | 10/2008 | Lewis | A61N 5/0613 607/91 |
| 2011/0306918 A1* | 12/2011 | Tsao | A61N 5/0616 604/20 |
| 2012/0116485 A1* | 5/2012 | Burgmann | A61F 13/023 607/90 |
| 2012/0289885 A1* | 11/2012 | Cottrell | A61N 5/0616 604/20 |
| 2013/0226269 A1 | 8/2013 | Eckhouse et al. | |
| 2014/0128942 A1* | 5/2014 | Bembridge | A61N 5/0613 607/90 |
| 2014/0303692 A1* | 10/2014 | Pignatelli | A61N 5/0613 607/89 |
| 2015/0290470 A1* | 10/2015 | Tapper | A61N 5/0616 607/91 |
| 2016/0114186 A1* | 4/2016 | Dobrinsky | A61L 2/10 607/94 |

* cited by examiner

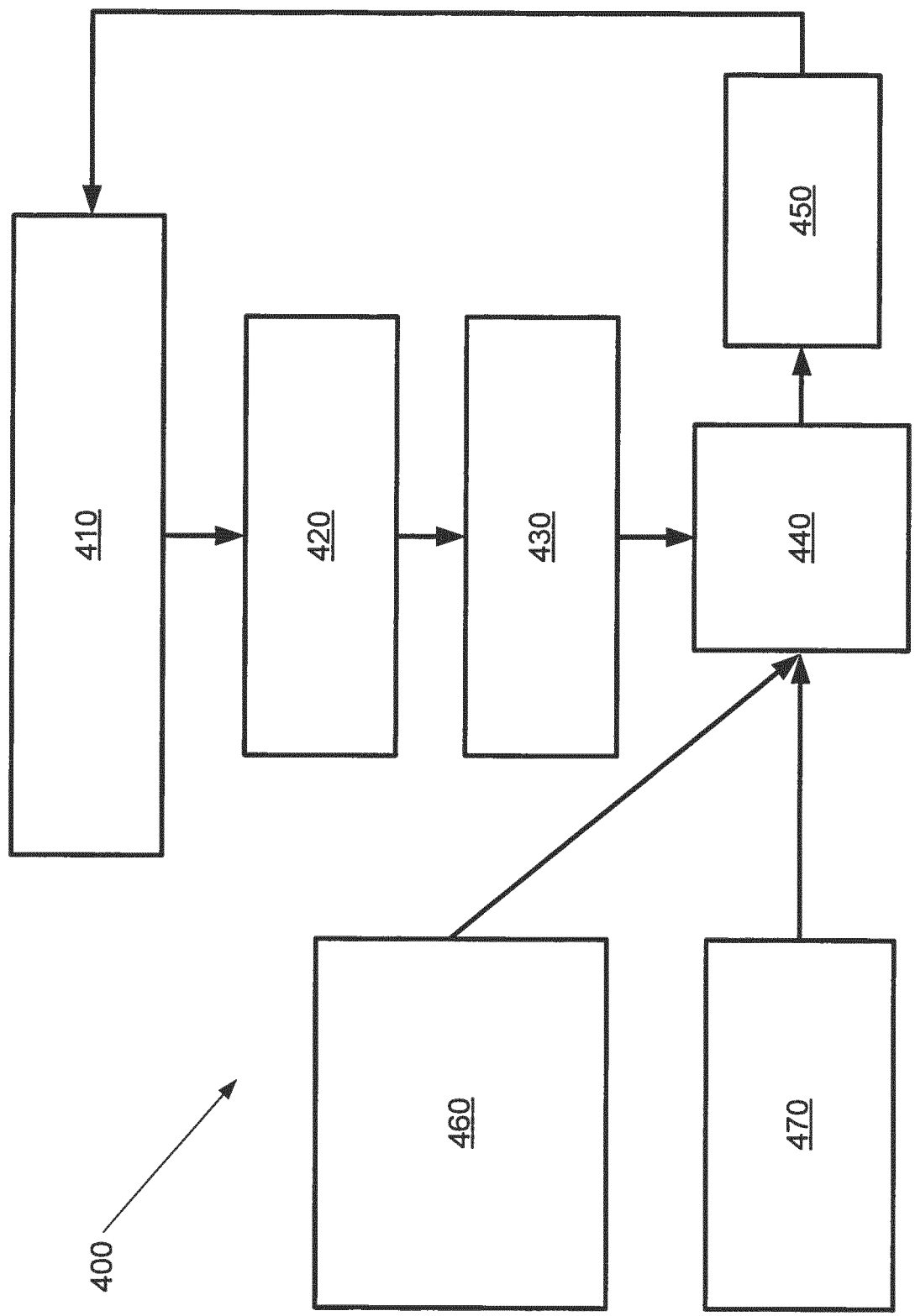

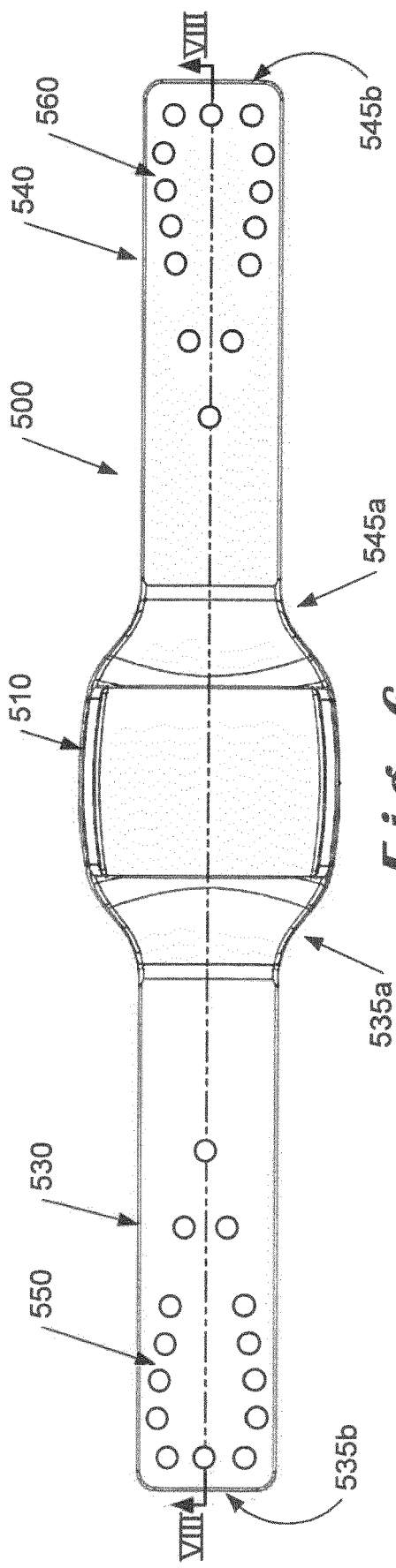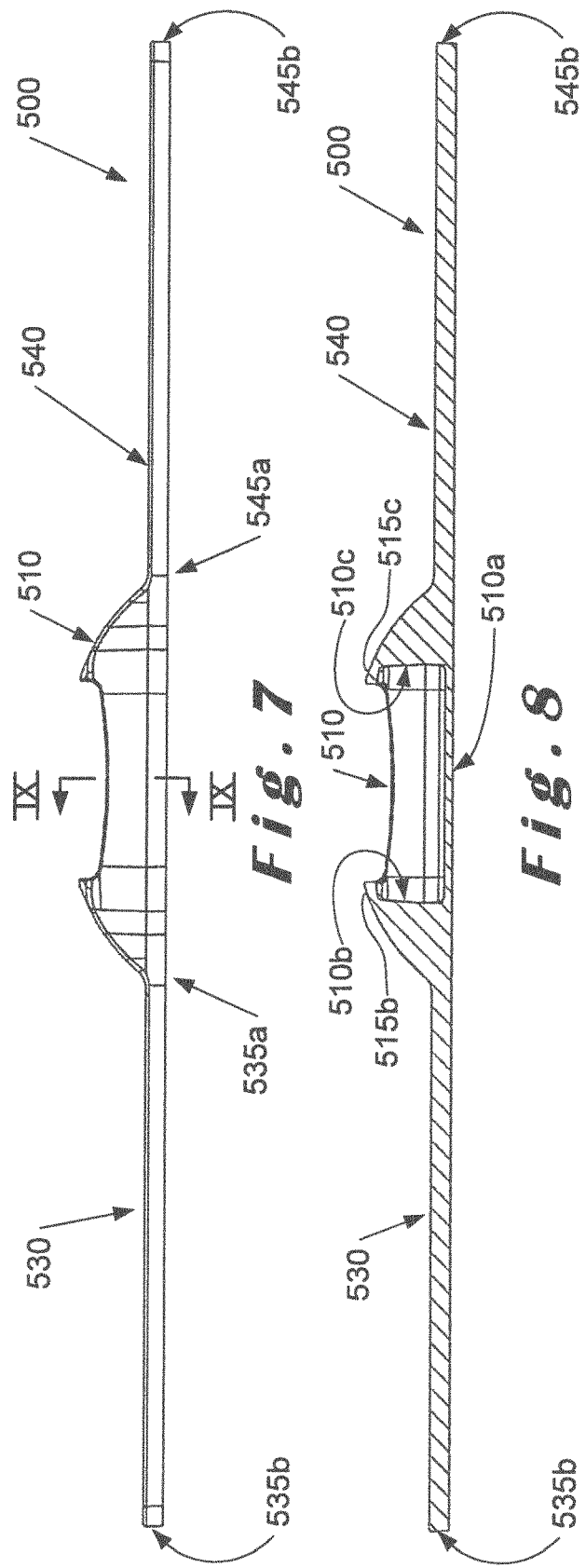

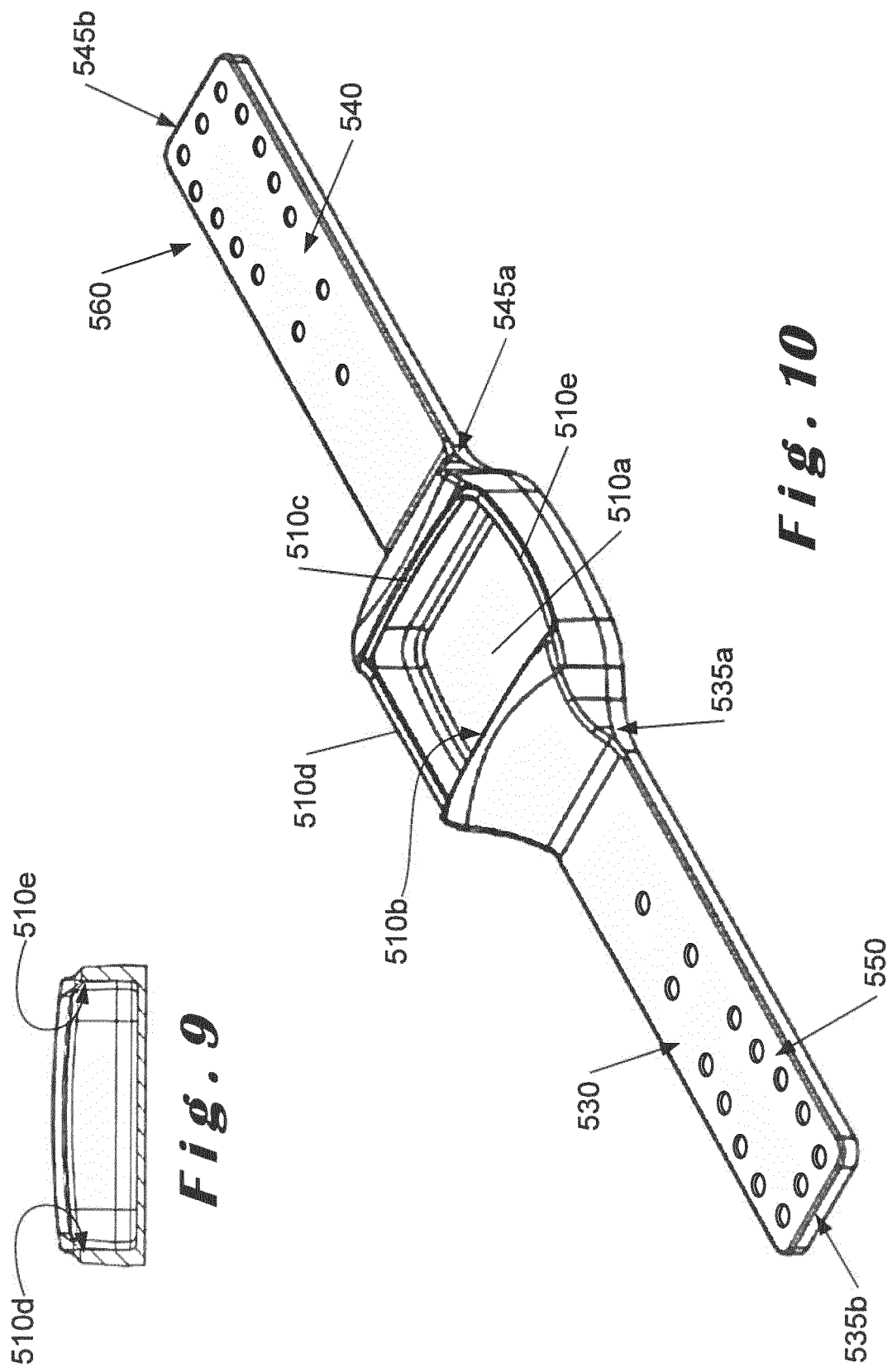

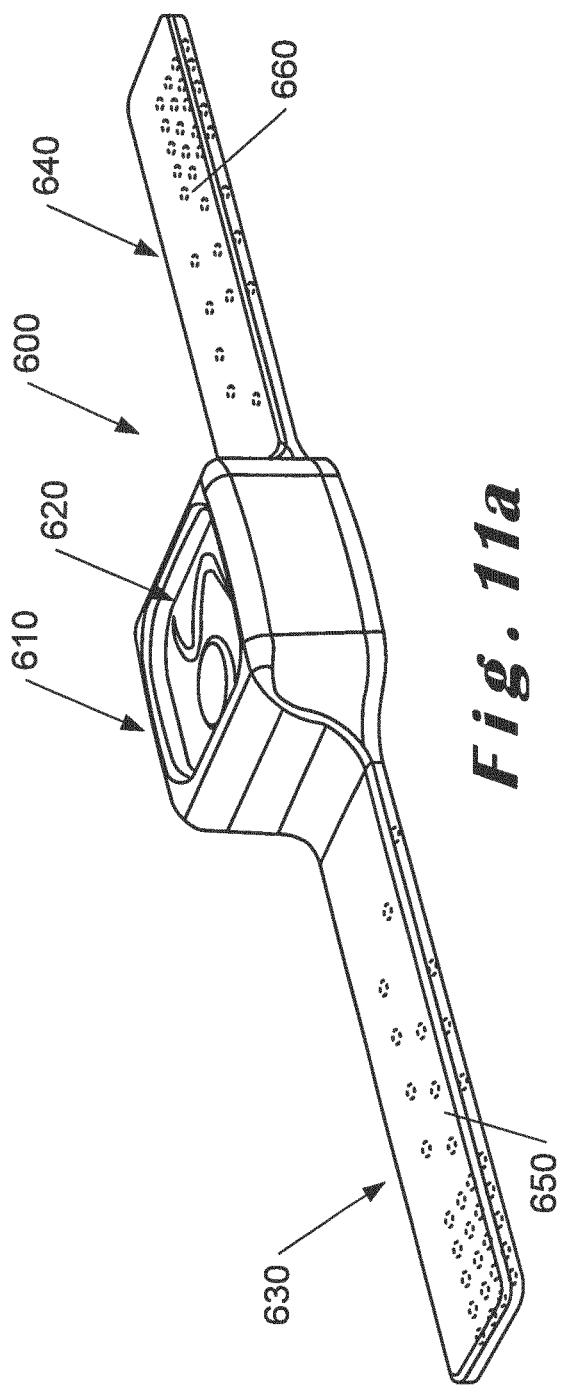
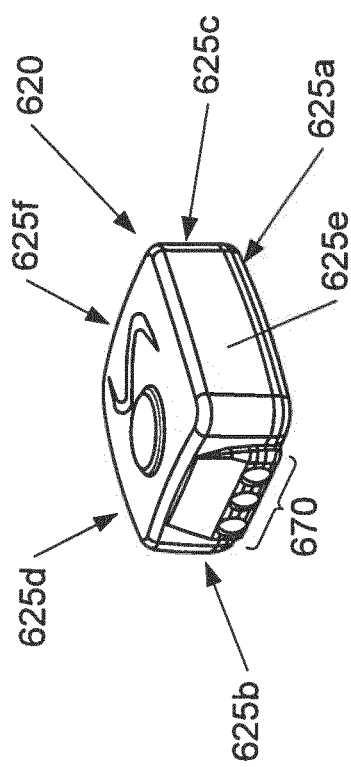

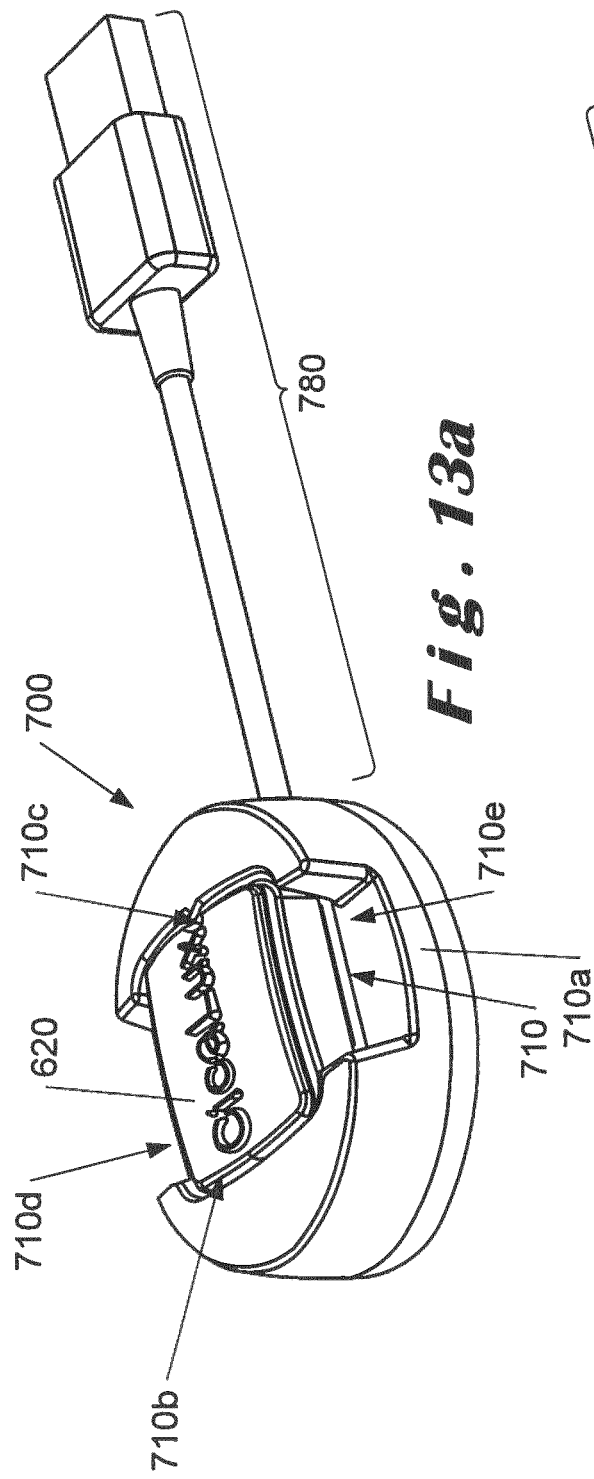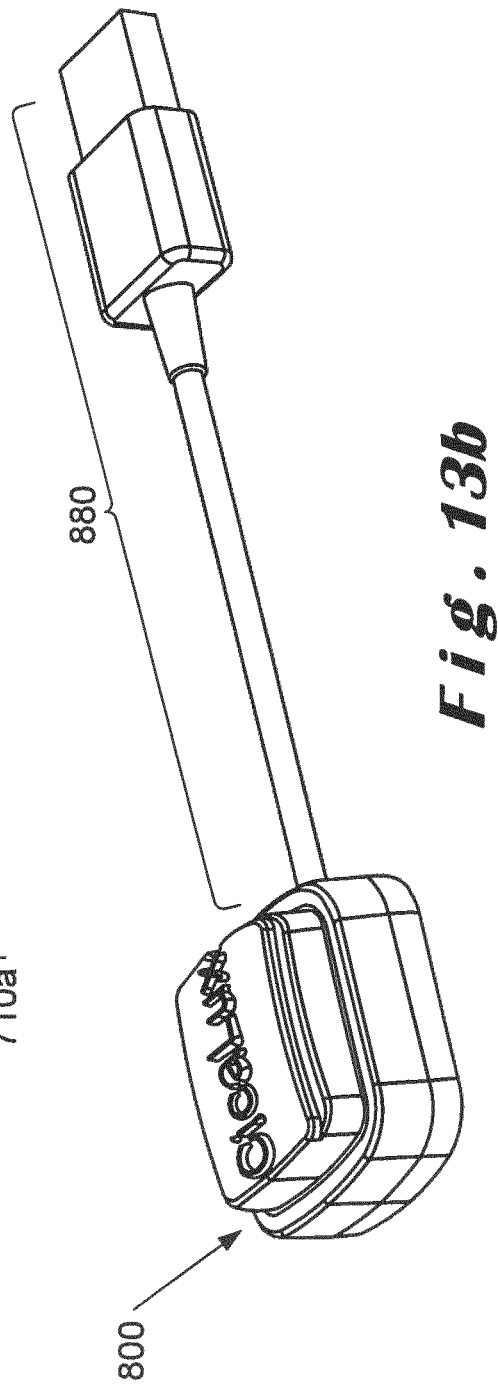

DERMAL REPAIR MANAGEMENT DEVICES

FIELD OF THE INVENTION

The present invention relates to improvements in or relating to dermal repair management devices, and, is more particularly concerned with bandages or sheets delivering both compressive hydration retention and low level light therapy to post-wound dermal tissue for improved healing and scar outcomes.

BACKGROUND OF THE INVENTION

It is estimated that one-third of all childbirths in the developed world are by Caesarian delivery (i.e. C-section). Worldwide, an estimated 20 million C-sections are performed each year. C-section is a surgical procedure used to deliver a baby through incisions in the mother's abdomen and uterus. These incisions can be anywhere from 10 to 15 cm long, and are generally made horizontally just below the pubic hairline. In rare cases, the incision is made vertically from below the belly button to the pubic bone.

Such long incisions tend to develop into a long scar over time for most women. Scarring is usually inevitable and the height, thickness, and color of the scarring will vary from woman to woman. Some will have a scar that will look red or pink for several months then fades to a pale, flat, thin line, and some women will have big, thick, raised scars.

An overwhelming majority of people are concerned with the aesthetic implications of a large scar, and, especially young women with C-section scars. Yet few receive medical attention or advice once the wound has closed after the first 10 to 14 days following surgery. Meanwhile, the last phase of wound healing called 'maturation' begins at this timepoint. This phase of scar development and remodeling will continue over the next several months.

Besides the negative aesthetic resulting in psychological pain, there are other medical worries related to post C-section scars, including physical pain. Some women feel pain or tightness in their scars when they are lifting, leaning, reaching or even standing up straight. If a woman cannot stand up straight without feeling pain or a "pulling" sensation, it may cause her to limit movement, change her posture, and eventually lead to pain in her body (for example, lower back pain). The scar can also cause muscle, connective tissue, and nerve damage in adjacent areas to the scarring. Over time, such damage can lead to pelvic pain, bowel problems (such as, constipation and irritable bowel syndrome OBS)) and painful sex.

To help reduce the risk of these unwanted outcomes, general advice given includes keeping the wound area clean, taking it easy, eating well, and avoid housework, lifting and big movements that might stretch or irritate the scar for the first six weeks. Some may also try topical creams and ointments, all which have varying success rates for promoting healing. Massaging on and around the scar area to promote blood circulation and better healing is also used and requires the necessary time and attention. However, the area around the scar, as well as the scar itself, may be very tender and painful to even a light touch, making it difficult to massage around the area. More invasive, costly, in-clinic options for scar management therapy include cortisone injections and cosmetic laser surgery.

The most commonly recommended product for use at-home as a first-line therapy is silicone gel sheets. Several studies have shown silicone sheets have positive benefits for reducing scar height and improving color. The 2001 International Advisory Panel for hypertrophic scar and keloid management concluded that silicone gel sheeting for hypertrophic scars, immature keloids, and mature keloids is a viable first-line treatment choice. The exact mechanism is unknown but most theorize the combination of compression and moisture retention of the oxygen permeable hydrophobic silicone plays a large role. Silicone sheets are widely available and are reusable and/or re-washable. The main drawback with such sheets is that they should be removed and washed once or twice per day. Besides the major user inconvenience of twice daily removal, washing, and placement, the sheet begins to degrade and develop foul odors.

Most silicone sheets are also excessively sticky rendering them very difficult to handle and wash thus leaving the potential of unwanted dead cells, dust, debris, bacteria, fungi to remain on the sheet on subsequent use. The silicone sheet should be replaced with a new sheet within 30 days of use, normally every two weeks for most brand although some silicone sheets may only last one week. To see scar improvement, silicone sheet therapy must be used daily for several months (often at least 4 months before any significant improvement is seen). These basic silicone sheets do not incorporate any advanced technology with anti-infective or pro-healing attributes to reduce risk/odor and accelerate treatment period respectively. Nor do they overcome the handling, washing and remaining debris headaches of excessive stickiness.

Light therapy has been researched as an effective treatment for a variety of dermal conditions including wound healing and scar management. In particular, researchers have shown accelerated and improved post C-section wound care and pain management with the use of infrared (IR) light therapy. The use of ultraviolet (UV) and safer blue light has also been widely researched for the reduction in bacteria as an anti-infective treatment.

Conventional light therapy normally requires a patient to sit near the light source (e.g. an IR lamp) at a prescribed distance from the bulky, non-portable, energy inefficient light source. Many patients (and their household members) find this therapy burdensome and inconvenient. As a result of the above issues, more proximal to the wound, light-emitting devices have been developed, for example, various form of light-emitting patches, which have improved on portability but these devices can still be quite bulky, and uncomfortable with extended wear time, and, are often in the form of one costly unit combining both bandage area with the power and control unit.

More recently, light bandages or patches containing several light-emitting diode (LED) lights have been introduced in recent years. Some bandages or patches incorporate LED light within the bandage area, and others have a single source LED with attached fiber optics that are deployed throughout the bandage. One such patch is described in US-A-2015/0335911 which comprises one or more fiber optic arrays which channel light in the form of one or more therapeutic illumination patterns and/or at one or more wavelengths. By using fiber optic arrays, complex glass structures of cladding over cylindrical cores are required which may have a detrimental effect on the type of light being used for the therapy.

However, as these bandage systems contain LEDs and wiring or attached fiber optics, they are not well suited for daily removal, washing and extensive manipulation before reuse. Moreover, there is a detrimental effect on using rigid or semi-rigid fibers and components across the sheet and against the skin where flexibility and softness is compromised and skin comfort may suffer. Nor does the bandage area have a detachable mechanism to allow it to be washable and/or manipulated prior to subsequent use. Thus, cost and convenience remain a hurdle in these designs. Often these designs are developed to provide deeper tissue, higher radiant or thermal energy, for a variety of conditions (e.g. arthritis), and, are limited to delivering only one light energy wavelength.

New methods and approaches are therefore desirable for delivering silicone bandage light energy therapy directly to the wound with alternating, edge-lit LED wavelengths (blue for infection prevention and odor/bacteria reduction and red/infrared (IR) for photo-bio-modulation and pro-healing during stage IV wound maturation and scar formation, while at same time keeping the silicone sheet material free of fibers/wires etc. that generally reduce the level of natural comfort provided to a user compared to a light sheet made only of soft, flexible silicone.

Moreover, the use of such bandages is not limited to C-section scars as there are over 100 million surgeries per year in the developed world with unwanted hypertrophic (raised) and keloid (raised and spread) scars which remain an issue for many patients. Other large incision surgeries resulting in substantial scarring include hysterectomies, breast reconstruction, breast augmentation, breast reduction, open heart procedures, kidney transplant procedures, etc.

There is therefore a need to provide a post-sealed wound, scar management system which overcomes the issues with presently used devices and which provides better, faster, more convenient, pain-free, odor-free, cost effective home wearable solution to the user.

SUMMARY OF THE INVENTION

It is an object of the present invention to provide a dermal repair sheet which can be worn by a user and to which radiation or light can be provided for treating a closed wound or scar.

It is a further object of the present invention to provide a dermal repair system which supplies radiation or light to the closed wound or scar by way of the dermal repair sheet.

The present invention is directed to a dermal repair sheet as defined by claim 1 and claims dependent thereon, a dermal repair system as defined by claims 25 and 26 and claims dependent thereon, and methods of treatment using the dermal repair system as define by claim 60 onwards.

By providing a small smart dermal repair system which can easily be correctly positioned to direct and distribute therapeutic radiation or light onto a closed wound or scar of a user, the benefits of combined silicone sheet or bandage and radiation or light therapy can readily be realized without the disadvantages of the prior art systems. In particular, due to a triple mode of therapy, red light/IR, blue light, and silicone compression with hydration, the dermal repair system of the present invention offers to improve the outcome for closed wound or scar healing.

Quadruple modes of therapy may also be provided with such a small smart dermal repair system. Such a system may comprise red light/IR, blue light and silicone compression together with the use of a tension-reducing light-reflective white tape as described in more detail below.

A multi-use smart light control unit (hereinafter referred to as simply "control unit") comprises at least one rigid, semi-flex or flex printed circuit board (PCB) encapsulated by a soft body or housing, for example, silicone. At least one radiation or light source is mounted to the PCB and configured for providing light energy to the dermal repair sheet. A microcontroller component is also mounted on the PCB and configured for controlling the operation of the at least light source.

At least one energy source is mounted within the body or housing on the PCB and configured for supplying power to at least the radiation or light source and the microcontroller component. The energy source may include non-rechargeable or rechargeable lithium coin batteries, or alternatively, rechargeable thin film micro-batteries. This has the advantage of providing a compact self-contained device.

In another embodiment, the batteries may be non-rechargeable lithium coin batteries and the housing of the control unit is adapted to be opened for the replacement of the batteries.

In one embodiment, the battery (and/or a PCB circuit to which the battery is connected) is connected to a port or battery contacts in the body of the control unit, the port or battery contacts being connectable to contacts formed in a base station recharger (or simply recharger station). In a further embodiment, this recharger station contains a cable, for example, a USB cable, for further connection to a power source for 'wired' recharging of the battery. In another embodiment, the USB cable can be used for data transfer between the control unit and programming thereof. The port is also connected to the microcontroller component via the PCB.

In an alternative "wireless" or non-contact embodiment, an antenna or inductive coil is at least partially mounted on the PCB and connected to the microcontroller component, the antenna or inductive coil being configured for at least receiving external signals and for passing them to the microcontroller component. Signals may also be transferred out of the body or housing using the antenna or inductive coil. Power is provided to the rechargeable battery by near-field or inductive coupling through the antenna or inductive coil. By mounting the antenna component within the control unit, a more efficient, coil can be formed for providing near-field or inductive coupling with external sources for the transfer of data to and from the microcontroller component. In addition, the antenna or inductive coil may be used for supplying energy for powering the components within the control unit, either directly or by way of a rechargeable battery.

In a further embodiment, conventional capacitive coupling may be used, but will not be described here in detail. Other forms of wireless power transfer methods may also be used, such as, microwave coupling and light wave coupling.

A male connector component extends from the control unit allowing for the insertion and 'coupling' of the radiation or light source (with limited air space to maximize radiant flux capture) to a female receptacle on the dermal repair sheet. It will be appreciated that the connectors may be the other way around provided they are complementary.

In one embodiment, the male connector component comprises a solid control unit which engages with a housing section formed between two sheet sections similar to a watch. Here, the housing section comprises a female receptacle or nest housing on the dermal repair sheet, and, the housing section is configured to hold the control unit in alignment such that the radiation source is aligned with the sheet sections on either side of the housing section.

In one embodiment, there is a single male connector which may be adapted to receive more than one wavelength of radiation or light, for example, IR and blue, for alternating dual therapy. In another embodiment, there is a male connector for each wavelength which still provides for alternating dual therapy.

The dermal repair sheet is constructed to allow the diffusion of radiation or light there-through with additional structured ? layers or patterns for further enhancing uniformity in the radiation or light diffusion. Such structure layers may include cladding, gratings and/or reflective layers.

In one embodiment, the control unit comprises a "biconvex" optically clear coupling lens or component attached to the at least one radiation or light source and configured to direct more light into the dermal repair sheet and to the dermal surface of a user when in position thereon.

In another embodiment, the control unit further comprises one or more sensor components connected to the PCB (e.g. the sensor component being configured for tracking temperature, force and movement, and radiation or light generated by the at least one radiation source). Typically, such sensors comprise a thermometer, a strain gauge, and an accelerometer which determines user adherence to therapy (i.e. when the device is being worn as well as determining if it is being worn at all). In addition, the strain gauge can measure stresses at or near the closed wound or scar site.

Naturally, other sensor types may be implemented on the dermal repair sheet, for example, biosensors including analytes for detecting viruses, bacteria, toxins etc. around the closed wound. Alerts may be provided by the control unit when the dermal repair sheet needs to be cleaned. Moisture content can be measured and/or monitored using a hygrometer or a humidity sensor to ensure that the tissue being treated remains sufficiently hydrated. Dedicated electrodes can also be incorporated for impedance spectroscopy measurements of the skin or tissues evolution.

In some embodiments, sensor contacts at the base of the control unit may extend through the dermal repair sheet and touch the skin directly.

Whilst it is preferred that the radiation or light source(s) operate at certain wavelengths, such light components may comprise one of the following: at least one solid-state light emitting diode, at least one organic light-emitting diode; at least one quantum dot light-emitting diode. A light-emitting diode (LED) may comprise two different LED emitters in one case. There are two types of these: one type where two dies are connected to the same two leads antiparallel to one another where current flow in one direction emits one color, and current flow in the opposite direction emits another color; and another type where two dies have separate leads for each die and another lead for common anode or cathode, so that they can be controlled independently.

The dermal repair sheet may also incorporate a phosphorescent particle, such as, strontium aluminate and enhancements or derivations thereof, that excite and glow for a period of time without any power source in order to extend battery life and provide continued therapy.

The main wavelength ranges are in the red-infrared region, between 600 nm and 1 mm, and in the blue-green region, between 430 nm and 570 nm. Typical total daily output dosages of between 0.1 $J/cm^2$ and 4 $J/cm^2$ are recommended.

In one embodiment, the radiation or light source is programmable, and can be controlled to operate in accordance with a predetermined program including duration, intensity, frequency of operation, wavelength etc.

In another embodiment, the radiation or light source emits a periodic pulse corresponding to an activation waveband of a photo-pharmaceutical compound (chemotherapy drug) disposed at a treatment site within the dermal tissue for treating skin cancers. (e.g. blue light).

In another embodiment, the radiation or light source acts as an on/off switch (e.g. blue light on, orange light off) to stimulate or suppress cell activity in specific cells containing light sensitive proteins (field of opto-genetics).

In an embodiment, the dermal repair sheet is configured to focus light, when in-situ on the user's sealed skin wound or scar.

The microcontroller component may comprise a wireless module configured for communicating wirelessly with an external controller, the external controller being configured for at least programming the microcontroller to control the light source.

In an embodiment, the antenna or contactless component interfaces with a recharger station and is configured to recharge the energy source component.

In another embodiment, the control unit has metallic contacts which connect directly with contacts in the recharger unit or station.

At least one further sensor component configured to measure the luminance of the light or radiance source may be provided. The microcontroller component may include a memory component which is configured to store data measured by the at least one sensor component.

In an another embodiment, the sensor may be incorporated in the base station for periodic calibration and/or monitoring of the dermal repair device, for example, before treatment. Such a sensor may comprise a photodiode array, or other light or radiance detecting/measuring system, configured to measure and/or monitor the light emission from the light or radiance source for strength and uniformity of emission. If the light or radiance source does not meet predetermined threshold values, the control unit may need to be replaced.

It is preferred that the body or housing of the control unit comprises a soft, flexible, conforming, biocompatible material that encompasses all components of the device. In one embodiment, the biocompatible material comprises silicone rubber.

In another embodiment, the body or housing of the control unit comprises a semi-rigid or rigid plastics material. A metallic housing can also be used. The semi-rigid or rigid body or housing can readily be accepted within a soft silicone nest formed in the dermal repair sheet between two sheet sections, or on the side of a single sheet section, as described above.

In another embodiment, either or both body components (control unit and dermal repair sheet) have their outer surface treated with an anti-microbial coating.

In order to direct light from the light or radiance source more efficiently, the male connectors of the control unit and the surface area surrounding the light source may include at least one portion which comprises a solid screen for at least inhibiting light from passing through that portion. Alternatively or in addition, the male connectors and the surface area surrounding the light source may include at least one surface coated with a reflector mirror film.

For the 'nest' embodiment where the control unit is removably mountable in a housing section of the dermal repair sheet, as the material is substantially transparent to the radiation being emitted from the control unit, radiation or light can be directed by the use of shields provided on a part of the housing section. In this embodiment, white reflector film may be used to direct the light or radiation down through the optically clear base and through the silicone sheet.

The control unit may comprise at least one photovoltaic cell portion for energy harvesting of ambient light. Each photovoltaic cell portion may comprise a connection with the energy source component.

The control unit may comprise one kinetic energy harvesting element for kinetic energy harvesting from walking and related body motion.

The control unit may comprise a thermo-generator harvester to recharge the energy source from body heat.

In accordance with another aspect of the present invention, the dermal repair system further includes a base station which comprises a recharger dock for recharging the energy source component of the control unit. In this embodiment, the dock may be further configured for programming the control unit.

The recharger station may recharge the energy source (e.g. battery) of the control unit by a wired connection (e.g. USB or direct metallic contacts linking the control unit to the recharger unit or station), or, without contact using RF or magnetic fields, e.g. by near-field or inductive coupling.

In one embodiment, the recharger station comprises a storage and cleaning (including ultrasonic capable) container or pod into which the entire system (both control unit and dermal repair sheet) is placed when not in use.

In its simplest embodiment, the control unit does not require wireless recharging or programming. Upon detaching the dermal repair sheet, the USB port becomes free for direct connection via USB cable to a laptop (the laptop providing recharging, programming and data download); or to smartphone (where smartphone is used for programming and data download).

Alternatively, the control unit may be directly plugged into wall outlet via a USB compatible outlet connector for recharging. In this case, the control unit is preferably in direct contact with recharger unit or station via metallic contacts. Moreover, the recharger unit or station preferably contains a USB cable for direct connection to a laptop for recharging, or direct connecting to a USB power adapter connected to a wall outlet.

The control unit may also incorporate a photodiode array, or more generally a light measuring device, to enable periodic verification and setting of the intensity and uniformity of the light emitted by the dermal repair system.

In another embodiment, a camera or smart phone camera could be used to to take a picture of the dermal repair system when emitting light and/or radiation. Suitable software may be provided on the camera or smart phone for analyzing the image to check intensity and uniformity of emission.

In accordance with a further aspect of the present invention, there is provided a method of treating recently closed wounds in which the control unit is attached to a dermal surface or dermis of a user and secured thereto by medical tape with the self-adhesive dermal repair sheet being placed over and onto the closed wound or scarred dermal tissue of the user. Once in position, radiation or light is directed onto the dermal tissue of the user from the dermal repair sheet.

Raised scars (both hypertrophic and keloid) can be treated in the same way.

The dermal repair system of the present invention provides many advantages over the prior art solutions for closed wound and scar therapy as will become apparent from the description below.

BRIEF DESCRIPTION OF THE DRAWINGS

For a better understanding of the present invention, reference will now be made, by way of example, to the accompanying drawings in which:

FIG. 1 or 2 is positioned;

FIG. 5 illustrates a flow chart showing how to use the dermal device of FIGS. 1 and 2;

FIG. 6 illustrates a view from the top of a dermal repair sheet in accordance with a third embodiment of the present invention;

FIG. 7 illustrates a side view of the dermal repair sheet of FIG. 6;

FIG. 8 illustrates a sectioned side view of the dermal repair sheet taken along lines VIII-VIII of FIG. 6;

FIG. 9 illustrates a sectioned end view of the dermal repair sheet taken along lines IX-IX of FIG. 7;

FIG. 10 illustrates a perspective view of the dermal repair sheet of FIG. 6;

FIGS. 11a and 11b illustrate a perspective view of a dermal repair sheet and a detailed view of the associated control unit respectively;

FIGS. 13a and 13b illustrate a round base station and a rectangular base station respectively for receiving the control unit for charging.

DESCRIPTION OF THE INVENTION

Figure 1:
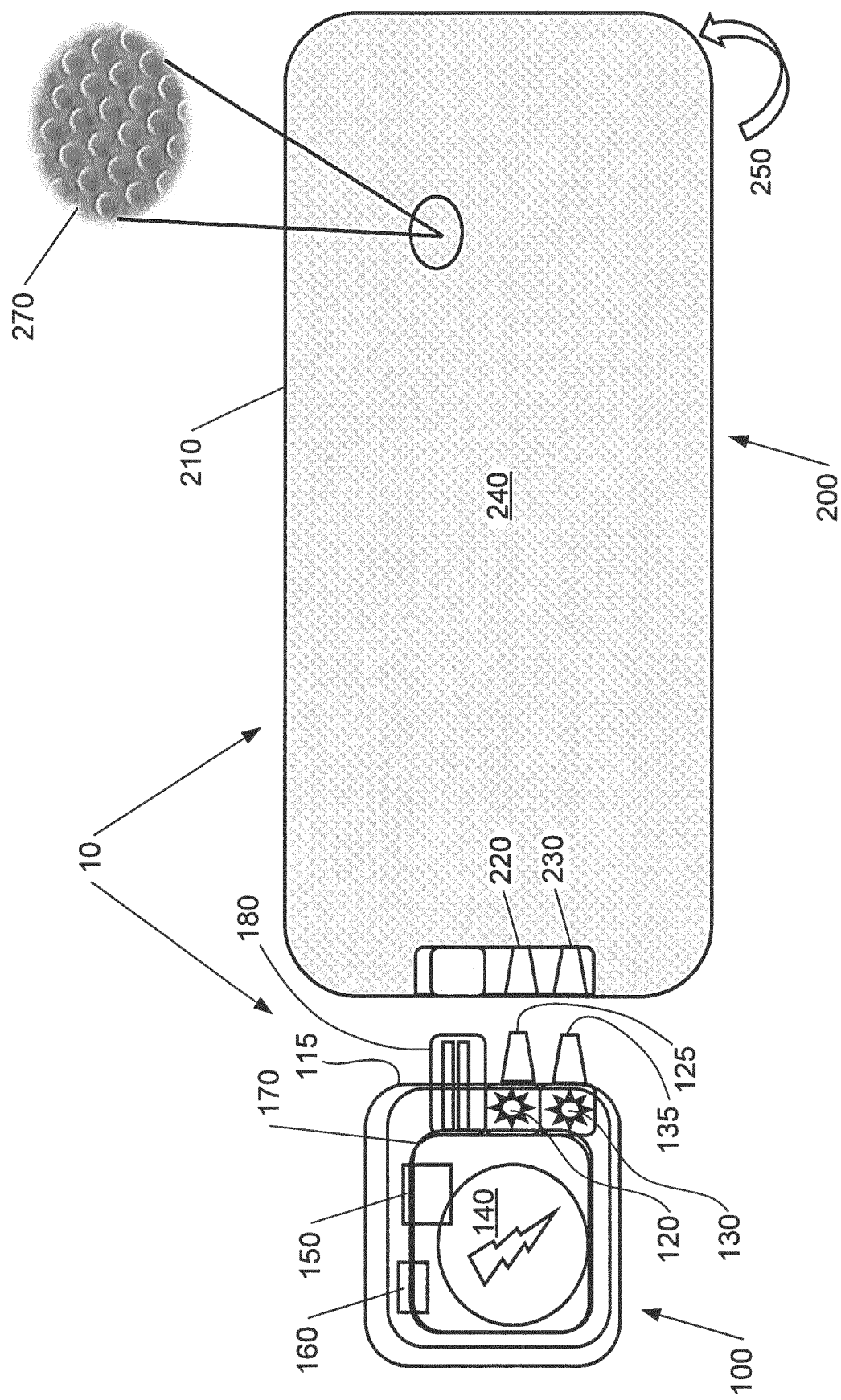
FIG. 1 illustrates a schematic front view of a dermal repair system for delivering radiation or light to a dermal surface in accordance with a first embodiment of the present invention.

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes.

The present invention relates to dermal therapy devices, materials and methods used to deliver low-level radiation to treat closed wounds and to reduce scarring. More specifically, a dermal repair sheet delivers both a compressive and hydrating biomaterial therapy combined with programmable low level light therapy (LLLT) for patients. Suitable wavelengths of radiation used, according to the particular treatment, range from blue light for reduced bacteria development, to red and infrared (IR) light for improved biomodulation and healing, and reduced fungi development (e.g. *C. albicans*).

The present invention provides a dermal repair sheet which can improve upon the benefits of basic silicone sheets by adding a programmable low level light control unit with efficient edge-lit light-guiding technology with planar diffusion elements to provide continuous therapy to a sealed wound for better, faster, safer and more convenient closed wound or scar management.

Silicone or polydimethylsiloxane (PDMS) belongs to a group of polymeric organosilicon compounds that are commonly referred to as silicones.

In one embodiment, there is an edge connector on the dermal repair sheet which is configured to engage with a complementary edge connector on the control unit. Radiation (or light) is directed from at least one radiation source to the dermal repair sheet through the engaged edge connectors.

In another embodiment, the edge connector is formed as a base nest connector within a housing section of a dermal repair sheet which is shaped to receive the control unit and has a complementary base connector formed therein.

By having an edge or base nest connector on the sheet or bandage and a complementary edge or base connector on the control unit, an interface is provided between the dermal repair sheet and the control unit when the two parts are connected. The complementary interface can easily be detached and re-attached to the control unit. This enables the dermal repair sheet to be removed for cleaning or replaced etc., as will be described in more detail below.

In one embodiment of the present invention, a dermal repair sheet which is removably connectable to a control unit, the control unit providing radiation (mainly in the form of visible or IR light) to the dermal repair sheet through an edge connector. Both the dermal repair sheet and the control unit are worn by a user when applying radiation or light therapy to a closed wound or scar. The dermal repair sheet is configured to have a textured or patterned first (upper) surface which forms a waveguide array for directing the radiation or light, provided to it by the control unit, in a more uniform way onto a dermal surface of a user.

As described above, the edge connector may form part of the base nest connector in the housing portion of the dermal repair sheet.

The dermal repair sheet may comprise a single- or multi-use, flexible, washable, detachable/re-attachable optically clear silicone gel or soft silicone sheet with a patterned surface for planar diffusion of radiation or light for a more uniform irradiance or illumination of the dermal tissue to be treated.

The pattern may be a structured multi-layered film, formed on a surface of the dermal repair sheet, which operates as a combination of more than one of: a waveguide core, its cladding, a grating and a reflector, in contrast to the two- and three-dimensional patterns known from the prior art. Alternatively, the pattern may be formed in a surface of the dermal repair sheet itself.

In this way, there is no need for fiber optic cables, wires or light strings—only a reflective layer or surface on one side of the dermal repair sheet and around its periphery together with a clear transparent adhesive layer on the other side of the dermal repair sheet and the edge connector arrangement between the dermal repair sheet and the control unit.

In one embodiment, the pattern may be graduated or graded across the dermal repair sheet from the edge-lit end to the edge furthest away therefrom. In this way, a gradient may be provided across the dermal repair sheet to manage the light scattering. For example, an almost smooth pattern (with less bumps or grating) may be provided closest to the radiation or light source and a more intensive pattern (with more bumps or grating) at the end of the dermal repair sheet furthest away from the radiation or light source, with the number of bumps or roughness increasing in a regular or non-regular fashion across the surface of the dermal repair sheet.

Alternatively, this pattern could also be in the form of a teardrop design which maximizes the balance and uniformity of the light across the surface of the dermal repair sheet. The teardrop design may be formed by appropriately placed dimples as described in more detail below.

In this way, more uniform radiation or light diffusion can be provided from the edge-lit LED source to the entire sheet surface, while, at the same time, allowing the dermal repair sheet to be trimmed and cut to size without much of an adverse effect on the radiation or light distribution uniformity across the entire sheet.

The dermal repair system of the present invention will be described in more detail as applicable to a C-section closed wound or scar. In this case, the system is positioned on the lower abdomen dermis, and, due to its position, it is possible to accommodate a slightly thicker control unit than conventional 'sheet-only' scar management devices. In addition, the dermal repair sheet only needs to be transparent or translucent in regions through or from which light is to be delivered to the dermis, and it can be optimized for light propagation at the wavelengths to be used for LLLT.

Components or elements which are the same have the same reference numbers throughout the Figures and the following description.

In an embodiment illustrated in FIG. 1, a front view of a dermal repair system 10 in accordance with the present invention is shown. The system 10 comprises a control unit 100 and a dermal repair sheet 200 which are connected to one another by way of an edge connector formed in an edge of the dermal repair sheet and a complementary edge connector formed in an edge or face of the control unit 100 as will be described in more detail below.

The control unit 100 comprises a housing 110 in which a pair of low-level light sources 120, 130 are mounted. At least one energy source 140, a microcontroller 150, and an antenna 160 are also mounted within the housing 110. The low-level light sources 120, 130, the at least one energy source 140, the microcontroller 150 and the antenna 160 are connected to, or directly mounted on, a printed circuit board (PCB) 170.

It will readily be understood that, although there is a pair of low-level light sources in the illustrated embodiment of the present invention, a single light source and more than two light sources may be implemented in other embodiments of the invention in accordance with the particular application.

The terms "light source" and "light sources" are intended to refer to a source that is capable of emitting radiation in either the visible (blue, green or red) or invisible (infrared (IR) or ultraviolet (UV)), and, is not limited to the emission of visible light.

A sensor element, for example, in the form of a temperature sensor and/or strain gauge sensor (described with reference to FIG. 2), may also be provided. Such a sensor element may form part of the microcontroller 150 or may be a separate component on the PCB 170 and connected to the microcontroller 150 for providing signals thereto in accordance with measurements taken. Other sensor elements, for example, photometer, accelerometer, hygrometer or radiometer, may be implemented.

It will readily be appreciated that the strain gauge is not essential but is desirable to measure influential forces (e.g. tensile (pull)-compressive (push) when a user is wearing the dermal repair system. In this way, the strain gauge provides signals which indicate a) whether the dermal device is being worn, and, b) whether the wound/scar area is experiencing abnormal tensile forces affecting scar formation and outcomes. Other low cost, and low power sensor elements may be provided, for example, for measuring the overall mobility of the user through an accelerometer, or for measuring temperature to provide an indication when the device was being worn on dermis by user, or for measuring moisture or humidity.

The housing 110 comprises a soft material. The soft material may be any moldable polymer that is above its gas transition temperature at 35 degrees C., and has naturally hydrophobic properties to prevent water ingress into the housing 110 thereby preventing damage to the components mounted or housed therein. Suitable materials include, for example, a soft, flexible, silicone rubber or acrylic elastomer.

The outer surface of the housing 110 may be treated with an anti-microbial coating.

Additionally, the housing 110 may have a portion (not shown) comprising a solid screen for at least inhibiting light from passing through that portion, and/or at least one surface coated with a reflector mirror film (or simply white coating). The PCB may also have its bottom surface, that is, the surface facing the dermis, coated with a white reflector film.

Furthermore, the housing 110 may include at least one energy harvesting element, for example, a kinetic energy harvesting element for energy harvesting of user-device movement, a thermo-generator (TEG) harvester for harvesting body heat, or a photovoltaic cell for light harvesting. Each harvesting element is connectable to the energy source 140 through a power management circuit (not shown).

The light sources 120, 130 are located at one face or edge 115 of the PCB 170 and housing 110 and are connected to respective male connectors 125, 135 which extend through the housing 110 for attachment or coupling to corresponding female connectors in a dermal repair sheet as will be described in more detail below. This orientation of the light sources 120, 130 is commonly referred as an 'edge-lit' orientation for the dermal repair sheet, such that, when the dermal repair system 10 is worn on the dermis of a user, the light propagates through the specially patterned waveguide or surface formed on or in the dermal repair sheet 200 and down toward the dermis of the user. As described above, the pattern may be graduated from the edge-lit end to the remote end of the dermal repair sheet allowing it to be trimmed and cut to size.

As described above, the male and female connectors are complementary to one another and may be implemented in another way.

If the male and female connectors are molded from moldable silicones, the surface of each connector has the ability to wet a surface of another connector so that they conform to one another and eliminate air gaps and therefore radiation or light loss. This wetting reduces reflection losses at the interface between the male and female connectors so that optical output does not have shadows or bright spots.

At least one waveguide coupling lens-connector (not shown) may be provided to enhance the transmission efficiency from the light sources 120, 130 of the control unit 100 to the dermal repair sheet 200. Other optical elements may be used for directing the light more efficiently, such as, gratings, cladding and optical fibers and/or waveguides.

The light sources 120, 130 may comprise light-emitting diodes (LEDs), for example, solid-state LEDs, quantum dot LEDs (QLEDs), or organic LEDs (OLEDs), which are capable of emitting radiation or light in the visible and non-visible part of the electromagnetic spectrum, for example, in the blue/green light range between 450 nm and 550 nm for the antimicrobial treatment, and in the red/ infrared light range between 650 nm to 1 μm for the bio-modulation, bio-stimulated accelerated healing treatment, with the combined LEDs delivering up to 4 J/cm$^2$ of radiant energy to the dermal site.

The light sources 120, 130 may be programmable to emit radiation or light at one or more predetermined wavelengths, for one or more predetermined durations, and for one or more predetermined power levels or intensities in accordance with the radiation or light which is suitable for a user of the dermal repair system. In addition, the light source 120, 130 may be configured to focus radiation or light, when in-situ on the dermis.

The microcontroller 150 is in electrical contact with the light sources 120, 130 and the energy source 140 so that it can be powered by the energy source or control its recharge, and, control and communicate the programmable therapy to the light sources 120, 130. The microcontroller 150 may comprise at least one micro-integrated circuit or micro-chip.

The microcontroller 150 may comprise a wireless module configured for communicating wirelessly with an external controller (not shown in FIG. 1), the external controller being configured for at least programming the microcontroller to control the light sources 120, 130. The external controller may control at least one of: the wavelength (e.g. alternating between two wavelengths), patterns (e.g. binary coding such as found on television remote controls), duration (e.g. millisecond pulses to continuous minutes), and intensity (optical or radiant power) of the radiation or light generated by the light source 120, 130.

The microcontroller 150 may include a memory for storing therapy program instructions or data measured by sensor elements until the control unit 100 is being recharged when a transfer of data can take place between the memory and an external device, for example, a computer platform, such as, a tablet, smartphone or laptop. Desktop computers can also be used.

In one embodiment, the transfer of data may be made using a Wi-Fi (a trademark of the Wi-Fi Alliance) connection. In another embodiment, the data transfer may be made using Bluetooth (a trademark of the Bluetooth Special Interest Group). In both embodiments, the transfer of data may be automatic, semi-automatic or manual, when an appropriate connection has been made between the control unit 100 and the external device.

The antenna 160, in electrical contact with the microcontroller 150, is used for wirelessly recharging the energy source 140 through near field or inductive coupling, or radio frequency (RF) power transfer. The antenna 160 also enables the transfer of data between a remote base station or equipment (not shown) and the microcontroller 150. It will readily be appreciated that the data transferred may include a programmed therapy and patient adherence or wear time (to the microcontroller 150) and measurements taken by sensors, such as strain/force, temperature, acceleration, moisture/humidity or radiation or light power measurements, in the control unit 100 (from the microcontroller 150). Remote base stations or equipment, for example, remote recording and/or monitoring devices, are described in more detail below.

Whilst the antenna 160 may be mounted within the housing 110, PCB 170 may comprise a coil for inductive coupling at, for example, 13.56 MHz. Other antenna types are also possible, for example, single metal wires for radio frequency (RF) coupling at frequencies between 900 MHz and up to at least 2.4 GHz which penetrate less into human tissue. Planar antennas comprising two metal plates could be used where one plate acts as a shield to prevent radiation being directed towards the user.

It will readily be appreciated that capacitive coupling or the use of rechargeable coin cell or flex film batteries is also possible for supplying energy to the control unit circuit (MCU, LEDs etc.).

The housing 110 also includes a USB connector 180 mounted on an end face (not specifically referenced) to which a USB connector (not shown) can be connected for recharging of the energy source 140 and the transfer of data to/from the microcontroller 150. It will readily be understood that the USB connector 180 may be connected to the energy source 140 and the microcontroller 150 by means of the PCB 170. Alternatively, the housing may also contain metallic direct contacts for connecting to a USB enabled base station for recharging purposes only.

In a preferred embodiment, the housing 110 of the control unit 100 has a substantially uniform cross-section and is symmetrical about a longitudinal axis with typical dimensions as shown in Table 1 below:

TABLE 1

| Dimension | (mm) |
| --- | --- |
| Length | <30 |
| Width | <30 |
| Thickness | 5 to 10 |

It will readily be appreciated that other suitable dimensions are possible and the invention is not limited to the values provided above.

The dermal repair system 10 of the present invention also includes a dermal repair sheet 200 which is connectable to the control unit 100. The dermal repair sheet 200, in the illustrated embodiment, is substantially rectangular with rounded corners and having a periphery or peripheral edge 210.

At one portion 215 of the peripheral edge 210, edge connectors 220, 230 are provided for engaging with connectors 125, 135 associated with the light sources 120, 130. The dermal repair sheet 200 comprises an upper or first surface 240 and a lower or second surface 250, the lower or second surface being positioned against dermal tissue of a user and comprises an adhesive at least around its periphery but preferably across the entire surface. There could also be an overlaying white reflective tape with adhesive that substantially covers the entire dermal repair sheet and overlaps at the edges of the dermal repair sheet so that a perimeter of tape is adhered directly to the skin and further secures device to skin.

The upper or first surface 240 comprises a textured or dimpled pattern surface pattern to guide radiation or light from the connectors 220, 230 in a more uniform distribution onto the dermal tissue onto which the dermal repair sheet 200 is positioned. An enlarged view of one example of the textured surface pattern is shown at 270.

A breathable reflector layer (not shown) may be provided on the upper or first surface 240 to assist with the direction of radiation or light to the dermal tissue. In one embodiment, the reflector layer may comprise a multi-layer thin film which may also include a textured surface pattern which is the same as that of the upper or first surface 240 or which may be different and designed to assist with the distribution of radiation or light in a uniform fashion onto the dermal tissue. This reflector layer may also overlap over the perimeter of the dermal repair sheet so that a portion thereof directly adheres to skin and helps to secure the entire dermal repair sheet to skin.

Although the dermal repair sheet 200 is illustrated as being substantially rectangular, it will readily be appreciated that other shapes are possible provided an edge is provided in which the edge connectors 220, 230 may be provided.

The dermal repair sheet 200 may be customizable, that is, it may be cut to any size or shape as required providing a surface area of between 2 cm$^2$ and 20 cm$^2$, for example, and as long as the connecting edge portion 215 remains intact.

When the dermal repair sheet 200 is connected to the control unit 100 by means of the connectors 220, 230 and 125, 135 and in position on a user, the USB port 180 may lie within or over the upper or first surface 240 of the dermal repair sheet 200.

In addition to radiation or light generated by the light sources, phosphorescent and/or chemiluminescent materials or devices may be provided in or on the dermal repair sheet, including those containing strontium aluminate nanoparticles, and which are activated or triggered by the radiation or light sources. Strontium aluminate activated by europium, $SrAl_2O_4:Eu(II):Dy(III)$, is a newer material with higher brightness and significantly longer glow persistence.

Such materials or devices may be present either in the dermal repair sheet itself or provided in a coating or other layer formed thereon. Alternatively, particles of such materials may be mixed in with the silicone material prior to molding. Blue light may be used to excite these particles so that they glow.

Figure 2:
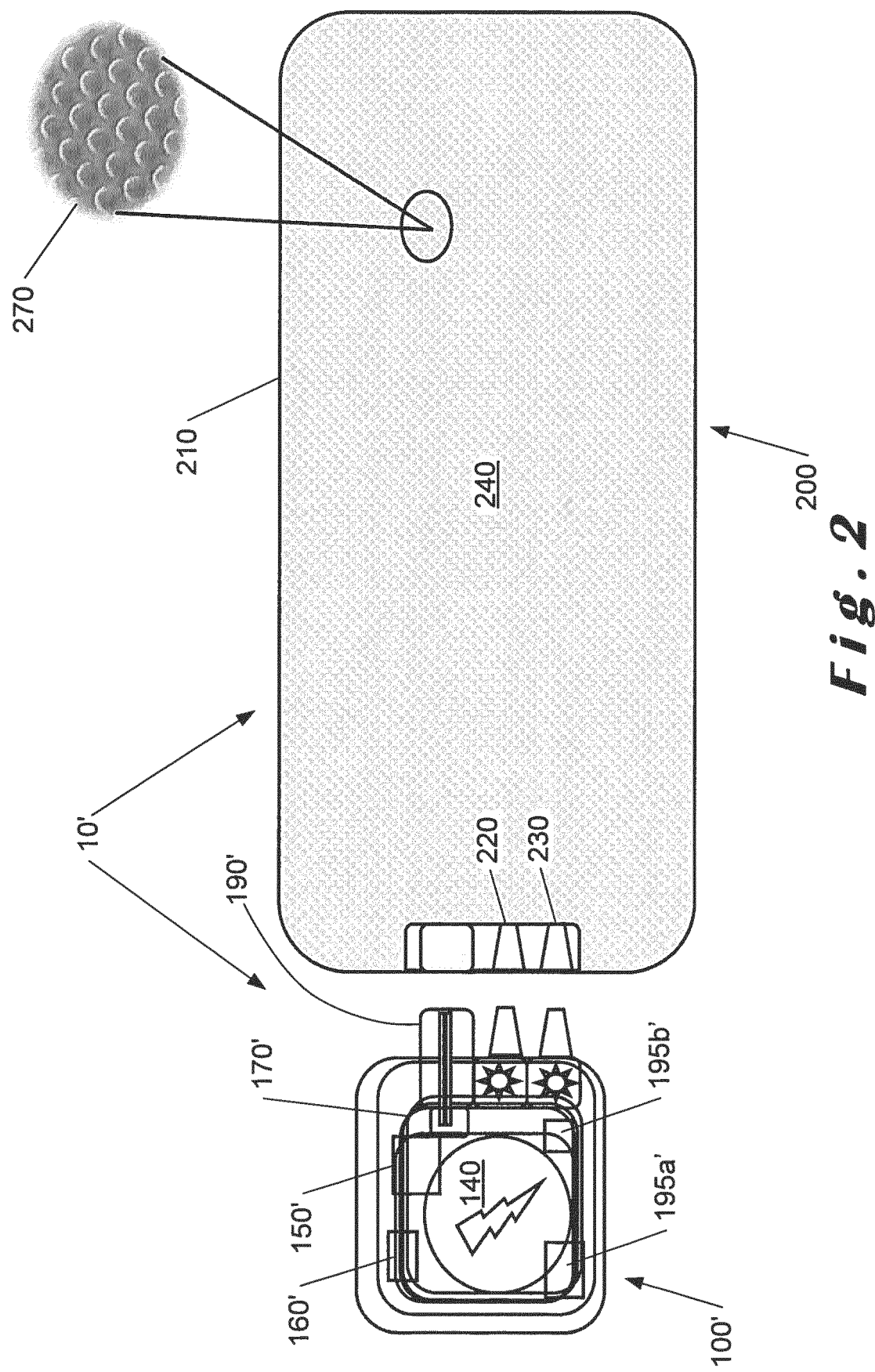
FIG. 2 illustrates a schematic front view of a dermal repair system for delivering radiation or light to a dermal surface in accordance with a second embodiment of the present invention.

FIG. 2 is similar to FIG. 1 and illustrates a second embodiment of a dermal repair system 10'. In the dermal repair system 10', a dermal repair sheet 200 is provided which is identical to that described above with reference to FIG. 1. A control unit 100' is also provided which is similar to control unit 100 but includes an antenna 160' in the form of an inductive coil. In this embodiment, the USB port 180 is replaced by, or incorporates in addition, a strain gauge 190' which measures push/pull forces between the control unit 100' and the dermal repair sheet 200. The measurement of these push/pull forces provides information relating to the healing process and also to user adherence/compliance to therapy.

Optional sensors 195a', 195b' are shown which comprise one or more of: an accelerometer and a temperature sensor for tracking user adherence/compliance to therapy and overall mobility. When at least the accelerometer is present, in conjunction with measurements obtained from the strain gauge, it is possible to determine if a user is taking it easy as instructed by doctor, or conversely, detrimentally overactive and mobile.

Figure 3B:
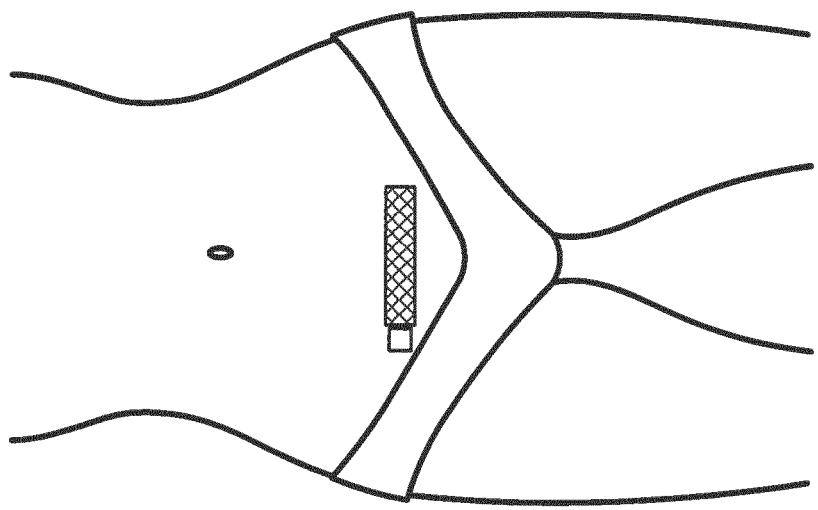
FIGS. 3a and 3b respectively illustrate a schematic front view of a female body with a C-section scar and the same female body on which the dermal repair system of either
Figure 3A:
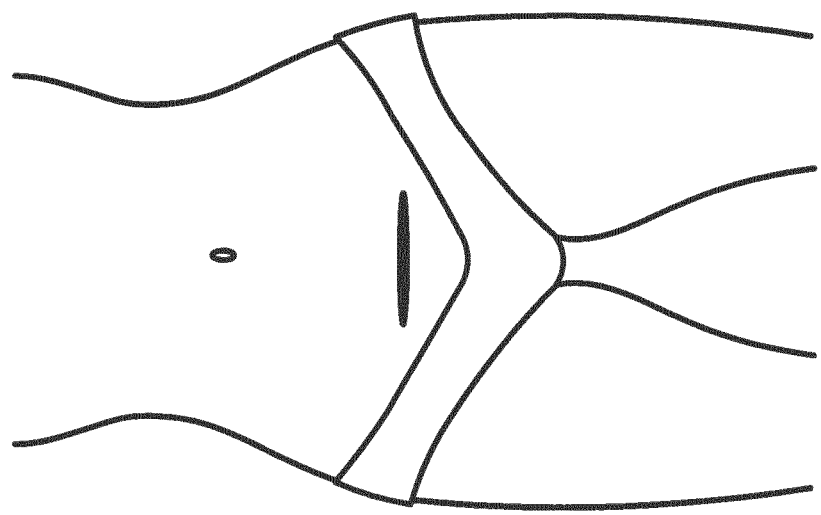

FIG. 3a illustrates a schematic front view of a user's mid-section with a C-section scar. FIG. 3b illustrates the location of the dermal repair system of FIG. 1 over the C-section scar in the most common location on the user (just below the pubis hairline) and the type (horizontal) of C-section incision most commonly performed. It will be readily appreciated that other dermal wound, surgical incision, and scar types and locations are possible and the invention is not limited to post C-section sealed wounds and scars only.

In addition, dermal repair sheets in accordance with the present invention may be used after breast reconstruction, and, it has been shown that certain wavelengths of light delivered to damaged nerves can rejuvenate nerve sensitivity and regenerate peripheral nerves.

Figure 4:
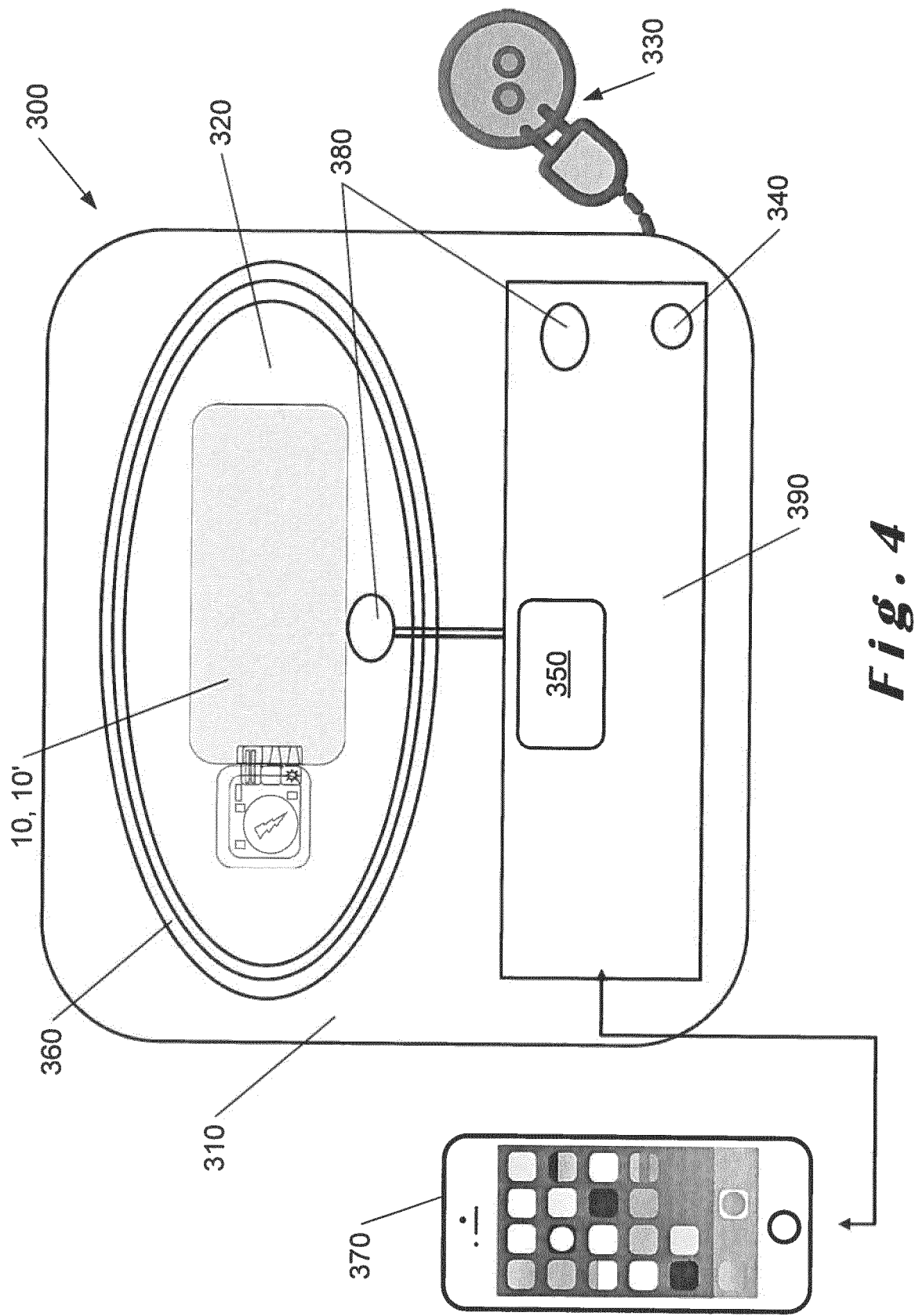
FIG. 4 illustrates schematically a base station for use with the dermal device of FIGS. 1 and 2.

Turning now to FIG. 4, a base station 300 is shown which comprises a housing 310 in which a receptacle 320 is provided for storing, cleaning, recharging and programming the dermal devices of FIGS. 1 and 2. The receptacle 320 may comprise a removable and replaceable case or the like.

Around the receptacle 320 is located an antenna or coil 360 by way of which the systems 10, 10' can be recharged and re-programmed wirelessly through RF and/or near-field induction as necessary. As shown, the antenna or coil 360 is connected to a PCB 390 incorporating a microcontroller 350 also provided within the housing 310. The base station 300 is connectable to a main power supply (e.g. a standard 110V/220V electrical outlet) as indicated by power cable 330 and includes an LED indicator 340 which indicates the status, that is, "recharging" and/or "ready".

The PCB 390 and microcontroller 350 is also connectable to a computerized system 370 for receiving programming instructions therefrom. In addition, the microcontroller 350 transfers readings from the dermal repair systems 10, 10' to the computerized system 370. The connection between the microcontroller 350 and the computerized system 370 may be wired via a USB-like cable or wireless using known wireless technologies, such as, Wi-Fi and Bluetooth. The computerized system 370 may also provide charging for the base station 300 by way of a USB cable (not shown).

The computerized system may comprise a desktop computer or a more portable device, for example, a laptop, a tablet, a smartphone, a personal digital assistant (FDA), or similar devices.

Once in the base station 300, the dermal repair system can be verified or calibrated to ensure that the radiation or light source still emits the correct wavelength range, intensity and uniformity through the dermal repair sheet 200 for a predetermined period of time, for example, up to 4 weeks before signaling that the dermal repair sheet 200 is too damaged or soiled for further use and a replacement dermal repair sheet 200 is required. A light meter or sensor 380 is incorporated within the base station 300, preferably mounted on the receptacle 320 and wire connected to the PCB 390, or alternatively, mounted directly on the PCB 390.

The dermal repair system as described above may be used for the treatment of sealed wounds and scars using directed radiation or light programmed to have a primary spectrum in the red-infrared region which can be adjusted to provide radiant energy and illuminance of predetermined intensity and time, for example, up to 4 J/cm$^2$ over a 24-hour period.

FIG. 5 illustrates a flow chart 400 illustrating use of the dermal repair system 10, 10' described above with reference to FIGS. 1 and 2. Starting from the dermal repair system in its base station 300 (as described above with reference to FIG. 4), the system 10, 10' is removed from the base station 300 (step 410) and activated for use (step 420). In some embodiments, the system 10, 10' auto-activates when removed from the base station 300. The system 10, 10' is then placed on the dermal wound or scar area of a user (step 430) using the adhesive layer on the dermal repair sheet 200 and medical tape for the control unit 100, 100'. A pre-programmed radiation or light therapy is applied to the dermal area (step 440). The system 10, 10' is then removed from the dermal area and returned to the base station for storage, cleaning and recharging (step 450).

Optional steps whilst the device is attached to the dermal area of the user include measuring and recording temperature using a sensor, for example, a temperature sensor, to determine adherence to the use of the device, with the use of a strain gauge that works by measuring the tensile stress between the dermal repair sheet 200 and the control unit 10' (as described above with reference to FIG. 2) correlated to the body's dermal tissue movements in the treatment area which may provide other data related to improving the therapy or explaining scar outcomes over time (step 460). In step 470, a single or multi-axis accelerometer may be used to detect magnitude and direction of the proper acceleration (or g-force), and can be used to sense orientation, vibration, shock, position of the device which would lead to important information about user activity, mobility, adherence, during therapy. Other sensors may be provided for measuring moisture and/or humidity, and, a time monitor may also be implemented to provide information relating to the time during which the device is worn.

Referring now to FIGS. 6 to 10, a further embodiment of a dermal repair sheet 500 in accordance with the present invention is shown. The dermal repair sheet 500 comprises a semi-rigid housing section 510 configured for receiving a control unit 620 (as shown in FIGS. 11a and 11b) and sheet sections 530, 540 each comprising a silicone light sheet.

In one embodiment, the control unit 620 includes at least one battery which may be either rechargeable, as described in more detail below, or non-rechargeable. In the latter case, the control unit 620 may be configured to be opened to allow the replacement of the non-rechargeable battery.

The housing section 510 is connected to sheet sections 530, 540 which have respective teardrop-shaped waveguides 550, 560 formed therein. In one embodiment, the housing section 510 and the sheet sections 520, 530 are formed of the same material and are preferably integrally formed as a single component as a single molding.

In another embodiment, the sheet sections 520, 530 may comprise a different material to the housing section 510. In such a case, the housing section 510 may be substantially opaque to the radiation or light being delivered by the LEDs in the control unit but having regions configured for allowing the transmission of the radiation or light from the LEDs to the silicone sheet sections 530, 540. The sheet sections 520, 530 may be molded to the housing section 510 to form the dermal repair sheet 500.

The dermal repair sheet 500 preferably comprises an optically clear flexible silicone sheet with a dimple teardrop patterned planar waveguide as will be described in more detail below.

As shown, each sheet section 530, 540 has a proximal end 535a, 545a and a distal end 535b, 545b with each sheet section being connected to the housing section 510 at its proximal end 535a, 545a.

For sheet section 530, the waveguide 550 is formed by a textured surface which comprises an arrangement of dimples which form the teardrop shape. In a preferred embodiment, a single dimple is formed nearer to the proximal end 535a of the sheet section 530 than to the distal end 535b thereof with pairs of dimples extending from the single dimple towards the distal end 535b thereof. Adjacent to the distal end 535b of the sheet section 530, three dimples form the "base" of the teardrop-shaped waveguide 550. As shown, the spacing between pairs of dimples increases with the distance from the proximal end 535a of the sheet section 530.

Similarly, sheet section 540 is configured the same way with a single dimple nearer to the proximal end 545a of the sheet section than to the distal end 545b thereof with pairs of dimples extending from the single dimple toward the distal end 545b of the sheet section 540.

Figure 12C:
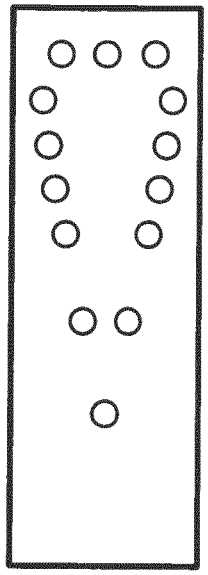
FIGS. 12a to 12c illustrate 'teardrop' formations for the dermal repair sheet of FIGS. 6 to 10.

In one embodiment, as shown in FIG. 12c, the first pair of dimples are spaced at 1 cm from the single dot with the single dimple being spaced 2 cm from the proximal end of the sheet section with the three dimples being spaced at 3 cm from the first pair of dimples and hence 6 cm from the proximal end.

The dimple pattern comprises a diffraction grating to direct the light towards the skin. The final row of three dimples act as a 'fence' to retain more light within the dermal repair sheet.

The housing section 510 is substantially transparent to radiation generated by the control unit 620 (FIGS. 11a and 11b) so that radiation can be directed through walls 510b, 510c of the housing section (510) and along the sheet sections 530, 540 by the teardrop-shaped waveguides 550, 560. As described above, the dermal repair sheet 500 comprises an optically clear flexible silicone sheet that forms the dimple teardrop patterned waveguides 550, 560.

As shown more clearly in FIGS. 8 to 10, the housing section 510 has a substantially rectangular base portion 510a which is surrounded by substantially perpendicular wall portions 510b, 510c, 510d, 510e which are designed to retain the control unit (not shown) securely within the housing section 510 of the dermal repair sheet 500. In effect, the housing section 510 can be considered to be a base nest (or female) connector with the control unit being considered to be a male connector which is configured to connect with the base nest when inserted in the housing section 510.

Wall portions 510b, 510c adjoining the proximal ends 535a, 545a of the sheet portions 530, 540 are configured to ensure that LED elements (not shown) can be aligned with the waveguides 550, 560. As the housing portion 510 is transparent to the radiation generated by the control unit 620, radiation or light from LEDs (as described below with reference to FIG. 11b), radiation or light passes through the wall portions 510b, 510c and along respective sheet sections 530, 540 to respective ones of the dimpled teardrop patterned waveguides 550, 560 which direct the radiation or light to the distal ends 535b, 545b of the sheet sections 530, 540.

Overhanging lip portions 515b, 515c are provided in respective wall portions 510b, 510c for retaining the control unit in correct alignment within the housing section 510, and, the configuration of the housing section 510 can be considered to form the base nest connector for the control unit.

In addition, each sheet section 530, 540 includes a full white reflective overcoat (not shown) which ensures that radiation is directed towards the associated waveguide 550, 560 and towards the distal end 535b, 545b of each sheet section 530, 540. The white reflective overcoat may be provided by white tape placed over the sheet sections 530, 540 to secure the dermal repair sheet 500 to the surface of the skin where it is to be used. Alternatively, the white reflective overcoat may comprise a layer coated over the upper surface (the surface furthest away from the skin) to reflect radiation or light downwards towards the waveguides etc.

Whilst an adhesive layer may be provided on the underside of the sheet sections 530, 540, that is, against the skin, to retain the dermal repair sheet 500 in position, after washing and drying etc., the tackiness of the adhesive diminishes, and medical tape can be used to hold the dermal repair sheet in position without causing too much skin irritation.

In a preferred embodiment, the silicone dermal repair sheet 500 has minimal tackiness and is held in place by white reflective medical tape that overlaps its edges around its periphery and secures the dermal repair sheet to the skin.

In another embodiment, where the dermal repair sheet is substantially larger than the closed wound on which it is being placed, the peripheral edges may be tackier than the rest of the dermal repair sheet to assist in retaining the dermal repair sheet in place over the closed wound.

Typical dimensions of the dermal repair sheet 500, given by way of example only, are shown in Table 2 below:

TABLE 2

| Dimension | (mm) |
| --- | --- |
| Overall length (distal end to distal end) | 150 |
| Length of housing | 42 |
| Width of housing | 26 |
| Length of each strip | 60 |
| Width of strips | 15 |
| Thickness of strips | 2 |
| Thickness of housing | 9 |
| Internal dimension of housing | 24 |
| Size of control unit | 25 |

Naturally, other dimensions are possible, and, the embodiment of the dermal repair sheet 500 described with reference to FIGS. 6 to 10 is not limited to these specific dimensions.

Figure 12A:
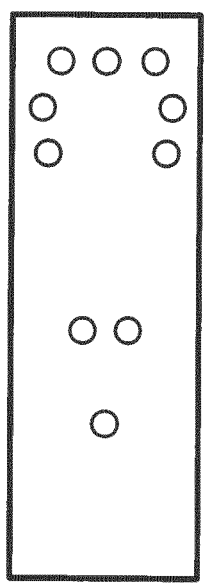
Figure 12B:
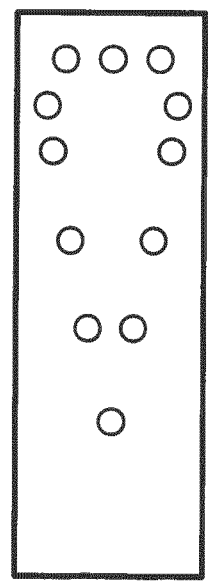

Other possibilities exist for the implementation of the patterned waveguides. For example, different arrangements of the pairs of dimples in a teardrop formation are possible as shown in FIGS. 12a to 12c and described in more detail below. In other embodiments, the dimples form a different formation.

As the dermal repair sheet 500 is intended to be re-usable, it is important that it can be washed to remove the build up of dead skin cells, hair, fabric lint, C. Albican fungi, bacteria etc.

In another embodiment, the dermal repair sheet may be subjected to ultraviolet (UV) or blue light to kill or inhibit bacteria and/or fungi thereon while the control unit is being recharged in its base station as described below. A separate enclosure may be provided into which the dermal repair sheet is inserted and the enclosure includes means for providing such illumination so that the illumination is isolated from the user.

In use, the dermal repair sheet 500 is positioned at a suitable location, that is, a location at which dermal therapy or repair is required, so that the radiation emitted from the rechargeable control unit reaches respective distal ends 535b, 545b of sheet sections 530, 540 of the dermal repair sheet.

FIG. 11a illustrates a dermal repair sheet 600 similar to that described above with reference to FIGS. 6 to 10 which is configured to receive a control unit 620 as shown more clearly in FIG. 11b. The dermal repair sheet 600 comprises a housing section 610 and sheet sections 630, 640, the sheet sections having respective dimple teardrop pattern waveguides 650, 660 formed therein.

FIG. 11b illustrates the control unit 620 in more detail. The control unit 620 is compact and includes the electronics for driving the LED(s) for providing radiation at the required wavelength. In one embodiment, the control unit 620 comprises a substantially rectangular base portion 625a having faces 625b, 625c, 625d, 625e and a matching cover portion 625f The base portion 625a is configured to mount the LEDs 670 (two or more adapted to be located adjacent opposing edges or sides 625b, 625c of the of the base portion 625a), a PCB (not shown) on which the electronics for controlling the LEDs 670 is provided, and one or more batteries (not shown) for powering the electronics and hence the LEDs 670.

In FIG. 11b, one set of three LEDs is shown in face 625b. However, it will readily be appreciated that another set of similar LEDs are also provided in face 625c. In other embodiments, each set of LEDs may comprise any suitable number of elements in accordance with the particular implementation.

The matching cover portion 625f may be sealed to the base portion 625a if the batteries are rechargeable so that a user does not need to open the control unit 620 for access to a battery compartment housing one or more batteries. Otherwise, the cover portion 625f may be removably connected to the base portion 625a to allow for the replacement of non-rechargeable batteries. In this case, no access to other components within the control unit 620 is provided.

The control unit 620 has typical dimensions as shown in Table 3 below.

TABLE 3

| Dimension | (mm) |
| --- | --- |
| Width | 24 |
| Length | 25 |
| Depth | 8.4 |

As the control unit 620 is configured to be mounted within the housing section 610 of the dermal repair sheet 600, it may be provided with markings additional to the LEDs 670 to indicate the correct orientation within the housing section 610.

As described above, the electronics etc. are powered by a battery housed within the control unit 620. In a preferred embodiment, the battery is rechargeable, and, the control unit 620 is mountable in a charging station (as described in more detail below) so that the battery can be recharged. The control unit 620 preferably includes a notch or other marker indicating the correct orientation thereof in the charging station.

In one embodiment, red light at 10 to 30 mW per LED can be provided with a single battery in the control unit for two one-hour phototherapy treatment sessions per 24 hours, the dermal repair sheet being cleaned and the battery recharged in between sessions.

In an embodiment with 6 LEDs each emitting between 10 mW to 30 mW, on average, 120 mW is supplied to the dermal repair sheet by the control unit.

In another embodiment, the battery in the control unit may provide one hour of 'ON' treatment per charge spread over the course of an eight to twelve hour total treatment time. The total treatment time may comprise an 'ON' time and an 'OFF' time for the application of light or radiation whilst the compression and hydration retention of the dermal repair sheet operates for this entire time. For example, the 'ON' time may be between 5 and 10 minutes at 6 to 12 cycles over the eight to twelve hours with the remaining time being 'OFF' time. The light or radiation may be applied in short pulses or may be continuous during the 'ON' time.

It will readily be appreciated that the control unit 620 may have at least some of the same functionalities as the control unit described above with reference to FIGS. 1 and 2 above, for example, programmable LEDs, one or more sensors, and an antenna for the transmission of data from the one or more sensors.

FIGS. 12a to 12c illustrate different dimple configurations for the waveguides formed in the sheet sections as described above with reference to FIGS. 6 to 10 and 11a. Whilst in each of FIGS. 12a to 12c, the dimples are concentrated at the base of the teardrop pattern, each pattern was shown to direct different amounts of light to the base of the teardrop. The most effective pattern was found to be that shown in FIG. 12c and shown in FIGS. 6, 10 and 11a.

As shown in FIG. 13a, a charging station 700 is configured for accommodating the control unit 620 for recharging if it has a rechargeable battery located therein. The charging station 700 is circular with a charging point 710 formed therein. The charging point 710 is of similar shape to the housing section 510 of the dermal repair sheet 500 and the housing section 610 of dermal repair sheet 600, and has a base portion 710a and two wall portions 710b, 710c with two open portions 710d, 710e which allow access for removal of the control unit 620 from the base station 700. The charging station 700 includes a USB connector 780 through which power is received for charging the rechargeable battery (not shown) in the control unit 620.

In this embodiment, the wall portion 710c includes a groove to allow for correct orientation of the control unit 620 within the charging station 700, the charging station having a complementary projection or protrusion which engages the groove in the wall portion 710c.

Electrical connectors (not shown) are provided in the base 710 of the charging station 700 which connect with electrical connectors on the base portion 625a of the control unit 620 for charging the rechargeable battery located therein. Markings (not shown) may be provided on one or more of the wall portions 710b, 710c and/or the control unit 620 to indicate the correct orientation of the control unit 620 in the charging point 710.

Although the charging station 700 is shown as being circular, it will readily be appreciated that other shapes are also possible, for example, the charging station may be rectangular or square with a similar charging point to that described with reference to FIG. 13a.

In another embodiment, as shown in FIG. 13b, a rectangular charging station 800 is shown which has a USB connector 880. The charging station 800 has a charging point 810 in the form of a well into which the control unit 620 is inserted. Electrical connectors (not shown) are provided in the charging point 810 of the charging station 800 which connect with electrical connectors on the base portion 625a of the control unit 620 for charging the rechargeable battery located therein. Markings (not shown) may be provided on the charging station 800 and/or the control unit 620 to indicate the correct orientation of the control unit 620 in the charging point 810. In one embodiment, the control unit 620 has a groove formed therein which is configured to engage a complementary projection or protrusion in the charging station to provide the correct orientation.

It will readily be appreciated that the dermal repair sheet described above provides a system in which radiation (infrared, red and/or blue light) is transferred along a silicone sheet providing compression. The addition of a tension light reflective white tape can be considered to provide a quadruple mode of therapy.

Although the dermal repair systems of present invention have been described for use solely as a combined compressive, hydration and radiation or light therapy systems, it will readily be appreciated that the device can be used in conjunction with other conventional therapies, such as, drug treatments, ointments, or injections.

It will be appreciated that the dermal repair system of the present invention may be used with therapies currently under preclinical and clinical investigation, for example, a periodic, programmed, pulsed, wavelength, corresponding to an activation and deactivation waveband of a photopharmaceutical compound (chemotherapy drug) or disposed at a treatment site on, within or below the dermal tissue of a user for treating skin cancers and other diseases and disorders.

It has been shown that photo-pharmaceutical compounds have been used for the treatment of skin cancer as described in US-A-2013/0178919. However, this is without using a dermal repair sheet in accordance with the present invention for evenly distributing the radiation or light over the surface of the skin being treated.

The programmable radiation or light source may act as an on/off switch (e.g. blue light on, orange/red light off) to stimulate or suppress activity in specific cells containing light sensitive proteins (field of optogenetics) for the treatment of certain diseases and disorders where the best access point is through the dermis.

It has also been shown that optogenetic based therapy using light having a wavelength of 505 nm may have tumor-reducing effects (http://www.pnas.org/content/111/17/6371.full).

The main benefits of the dermal repair system of the present invention may include, but are not limited to:
Adds smart, programmable low-level radiation or light therapy for improved outcomes
Greater convenience and reduced hassle
Shorter therapy time
Accelerates healing process to desired scar outcome
Anti-infection, anti-bacterial, anti-odor (blue light)
Pro-healing, photo-bio-modulation (red light/IR)
Sensors provide user adherence to therapy and stress data useful for correlating to therapy outcomes.
Sensors provide stress impact data.
Sensors provide user adherence to therapy and stress data useful for correlating to therapy outcomes.
Wirelessly programmable and rechargeable.
Wireless wear—no power or data cables attached to user body.
The control unit incorporates thin film energy technology, micro LED technology and wireless rechargeable features into a very small housing.
These benefits need to be weighed against the disadvantage of having to wear an additional control unit attached to the dermal repair sheet.
Main potential benefits compared to new LED light bandage technologies include but are not limited thereto:
Washable-water resistant control unit and bandage component which can be removed and submerged for cleaning.
Detachable/re-attachable dermal repair sheet with proprietary two-LED source connection and distribution system.
No LED Wires, electronics, fiber optics in dermal repair sheet component.
Edge lit system with planar light diffusion technology patterned into dermal repair sheet.
Cost-effective as dermal repair sheet is replaceable without discarding control unit.
Phosphorescent particle layer for improved power management and radiant energy efficiency.
Optical grade, flexible, soft-silicone dermal repair sheet allows enhanced light-piping performance.
The dermal repair sheet can be cut at certain indicated intervals and retain planar light diffusion performance.

The dermal repair systems described above address the concerns and limitations in the prior art to provide the following potential benefits:
Non-invasive (e.g. no steroid injections required)
Non-toxic light therapy (e.g. no drug-related side effects or allergic reactions due to chemical ingredients or compounds)
No pharmacological side effects such as irritation, pain, staining, itching due to toxins or preservatives.
Programmable for personalized treatment.
No negative aesthetic impact (worn under clothing) thus increasing patient adherence/acceptance rate.
Quick, easy and convenient to use—easily positioned and removed without medical intervention.
Safe and comfortable—thin, soft profile providing maximum safety, comfort and wear time.
Removable at will.
Rechargeable (eco-friendly power source)
Wireless (no tangling in wires or cables during use)
Mobility—can be used an here including at home and when traveling
Adaptable platform for additional LLLT therapies for other diseases and disorders
Smart phone—Bluetooth enabled and controlled.

It will readily be appreciated that the present invention is not limited to the specific embodiments described above, and that modifications and variations thereof may be implemented. For example, the embodiment of FIGS. 6 to 10, 11a and 11b may be modified to have only one sheet section connected to the housing section.

The invention claimed is:

1. A dermal repair sheet configured for supplying radiation to a dermal surface of a user to which the dermal repair sheet is removably attachable, the dermal repair sheet comprising:
a housing section which is configured for receiving a control unit;
at least one sheet section connected to the housing section, the at least one sheet section having a proximal end connected to the housing section and a distal end extending away from the housing section;
the at least one sheet section comprising a first surface having at least one peripheral edge and including a pattern configured for guiding radiation thereover to supply radiation to the dermal surface;
the at least one sheet section comprising a second surface formed on an opposite side of the first surface to the pattern, the second surface being removably attachable to the dermal surface, the second surface having an adhesive layer formed thereon and a release sheet configured for being releasably attached to the adhesive surface; and
an edge connector located in the housing section at the connection with the proximal end of the at least one sheet section and configured for connecting with the control unit for receiving radiation therefrom.

2. A dermal repair sheet according to claim 1, wherein the pattern on the first surface comprises a textured surface pattern configured to guide radiation from the edge connector and distribute the radiation on the dermal surface to which the dermal repair sheet is removably attached.

3. A dermal repair sheet according to claim 1, wherein the second surface includes a reflector configured for directing the radiation towards the first surface.

4. A dermal repair sheet according to claim 1, wherein the first and second surfaces are customizable to at least one of: a desired shape and a desired size.

5. A dermal repair sheet according to claim 1, further comprising:
an anti-microbial coating on the first surface.

6. A dermal repair sheet according to claim 1, wherein the at least one sheet section includes a dimpled pattern configured for generally guiding and distributing radiation from the proximal end to the distal end thereof.

7. A dermal repair sheet according to claim 1, wherein the dimpled pattern comprises a teardrop shape with an apex of the teardrop being nearer to the proximal end of the at least one sheet section than the distal end and a base of the teardrop being adjacent the distal end of the at least one sheet section.

8. A dermal repair sheet according to claim 1, wherein first and second sheet sections are connected to the housing section, the first and second sheet sections being configured to be symmetrical with respect to the housing section.

9. A dermal repair sheet according to claim 1, wherein the at least one sheet section and the housing section are integrally formed as a single component.

10. A dermal repair system comprising:
at least one dermal repair sheet configured for supplying radiation to a dermal surface of a user to which the dermal repair sheet is removably attachable, the dermal repair sheet comprising:
a first surface having at least one peripheral edge and including a pattern configured for guiding radiation thereover to supply radiation to the dermal surface, the first surface comprising at least one sheet section connected to a housing section, the at least one sheet section having a proximal end connected to the housing section and a distal end extending away from the housing section, the housing section providing an edge connector at the connection with the proximal end of the at least one sheet section;
a second surface on an opposite side of the first surface to the pattern, the second surface being removably attachable to the dermal surface, the second surface having an adhesive layer which extends over a substantial part of the second surface and a release sheet configured for being releasably attached to the adhesive surface; and
an edge connector located in the at least one peripheral edge configured for directing radiation to the first surface; and
at least one radiation source configured to be mounted in the housing section and configured for providing radiation to the at least one sheet section of the dermal repair sheet.

11. A dermal repair system according to claim 10, further comprising:
a control unit configured to be mounted within the housing section of the dermal repair sheet, the control unit including:
at least one complementary edge connector configured for cooperating with edge connector within the housing section of the dermal repair sheet;
a microcontroller component mounted in the control unit and configured for controlling operation of the at least one radiation source, the at least one radiation source being mounted within the control unit; and
at least one energy source component configured for supplying power to the at least one radiation source and to the microcontroller component.

12. A dermal repair system according to claim 11, wherein the at least one radiation source comprises at least one electromagnetic radiation source comprising at least one of: a solid-state light-emitting diode, an organic light-emitting diode, and a quantum dot light-emitting diode.

13. A dermal repair system according to claim 11, wherein the at least one radiation source emits light in a wavelength range of 430 nm to 570 nm.

14. A dermal repair system according to claim 11, wherein the at least one radiation source emits a red to infrared light in a wavelength range of 600 nm to 1 mm.

15. A dermal repair system according to claim 11, wherein the at least one radiation source emits a radiant flux of up to 50 mW/cm2 and delivers a spectral radiance up to 4 J/cm2 to the dermal surface of a user over a 24-hour period.

16. A dermal repair system according to claim 11, wherein the control unit further comprises at least one coupling lens configured for coupling the at least one radiation source to the dermal repair sheet.

17. A dermal repair system according to claim 11, wherein the at least one radiation source is programmable.

18. A dermal repair system according to claim 11, further comprising:
at least one sensor component mounted in the control unit, the at least one further sensor component being configured to measure at least one of: temperature of the dermal repair sheet, temperature of skin, stress forces acting on the control unit and/or the dermal repair sheet, hydration of skin, and adherence/compliance to therapy; and
wherein the microcontroller component includes a memory component which is configured to store data measured by the at least one sensor component.

19. A dermal repair system according to claim 11, wherein the microcontroller component comprises a wireless module configured for communicating wirelessly with an external controller, the external controller being configured for at least programming the microcontroller to control the at least one radiation source.

20. A dermal repair system according to claim 19, wherein the external controller is configured for controlling at least one of: a wavelength of the at least one radiation source, radiation emittance patterns, duration of radiation emittance and radiation flux generated by the at least one radiation source.

21. A dermal repair system according to claim 11, further comprising a recharger station configured to recharge the at least one energy source component.

22. A dermal repair system according to claim 21, wherein the control unit is rechargeable using a wired connection cable, the wired connection cable being configured for at least one of: programming and data transfer between the control device and an external device.

23. A dermal repair system according to claim 21, wherein the recharger station comprises a USB recharging pod, the USB recharging pod having metallic contacts configured for engaging corresponding metallic contacts on the control unit.

24. A method of treating a closed dermal wound, developing or having a scar, the method comprising:
placing a dermal repair system onto a dermal surface of a user; and
directing radiation onto and into at least an epidermal tissue layer of the user such that the radiation passes through the epidermal and dermal tissue to subcutaneous tissue of the user;
wherein the dermal repair system comprises:
at least one dermal repair dermal repair sheet configured for supplying radiation to the dermal surface of the user to which the dermal repair sheet is removably attachable, the dermal repair sheet comprising:

a first surface having at least one peripheral edge and including a pattern configured for guiding radiation thereover to supply radiation to the dermal surface, the first surface comprising at least one sheet section connected to a housing section, the at least one sheet section having a proximal end connected to the housing section and a distal end extending away from the housing section, the housing section providing an edge connector at the connection with the proximal end of the at least one sheet section;

a second surface on an opposite side of the first surface to the pattern, the second surface being removably attachable to the dermal surface, the second surface having an adhesive layer which extends over a substantial part of the second surface and a release sheet configured for being releasably attached to the adhesive surface; and an edge connector located in the at least one peripheral edge configured for directing radiation to the first surface; and wherein the dermal repair system further comprises:

at least one radiation source configured to be mounted in the housing section and configured for providing radiation to the at least one sheet section of the dermal repair sheet; and a control unit configured to be mounted within the housing section of the dermal repair sheet, the control unit including:

at least one complementary edge connector configured for cooperating with edge connector within the housing section of the dermal repair sheet;

a microcontroller component mounted in the control unit and configured for controlling the operation of the at least one radiation source, the at least one radiation source being mounted within the control unit; and at least one energy source component configured for supplying power to the at least one radiation source and to the microcontroller component.

25. A method according to claim 24, wherein the closed wound comprises one of: an incisional wound, a C-section closed wound, a hysterectomy closed wound, a hypertrophic scar and a keloid scar.

26. A method according to claim 24, further comprising: programming the at least one radiation source to emit radiation in at least one of: blue-green wavelength range and red-infrared wavelength range.

\* \* \* \* \*